US012721597B2

(12) United States Patent
Murakami

(10) Patent No.: US 12,721,597 B2
(45) Date of Patent: Sep. 1, 2026

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Hiroshi Murakami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 23 days.

(21) Appl. No.: 18/602,651

(22) Filed: Mar. 12, 2024

(65) Prior Publication Data

US 2024/0215950 A1 Jul. 4, 2024

Related U.S. Application Data

(63) Continuation of application No. PCT/JP2022/028429, filed on Jul. 22, 2022.

(30) Foreign Application Priority Data

Sep. 30, 2021 (JP) ................................ 2021-160708

(51) Int. Cl.
*A61B 8/00* (2006.01)

(52) U.S. Cl.
CPC ............ *A61B 8/4472* (2013.01); *A61B 8/461* (2013.01); *A61B 8/56* (2013.01); *A61B 8/58* (2013.01)

(58) Field of Classification Search
CPC ......... A61B 8/4472; A61B 8/461; A61B 8/56; A61B 8/58; A61B 8/54; A61B 8/565; A61B 8/00
See application file for complete search history.

(56) References Cited

U.S. PATENT DOCUMENTS

2006/0193287 A1* 8/2006 Ooshima ............... H04W 88/02 370/328
2007/0177520 A1* 8/2007 Morinaga ........... H04L 43/0876 370/252

(Continued)

FOREIGN PATENT DOCUMENTS

JP 2014-050648 A 3/2014
JP 5727785 B2 6/2015

(Continued)

OTHER PUBLICATIONS

International Search Report issued in PCT/JP2022/028429; mailed Sep. 20, 2022.

(Continued)

*Primary Examiner* — Alexei Bykhovski
(74) *Attorney, Agent, or Firm* — Studebaker Brackett PLLC

(57) ABSTRACT

An ultrasound diagnostic apparatus includes an ultrasound probe, and an apparatus main body wirelessly connected to the ultrasound probe, in which the ultrasound probe includes an image generation unit that generates an ultrasound image at a constant frame rate, a frame interval adjustment unit that adjusts a frame interval of the ultrasound image transmitted to the apparatus main body by skipping some frames of the ultrasound image transmitted to the apparatus main body per unit time in accordance with a transmission rate of the ultrasound image, and a probe side communication circuit that transmits the ultrasound image with the adjusted frame interval to the apparatus main body via wireless communication, and the apparatus main body includes a main body side communication circuit that receives the ultrasound image via the wireless communication from the ultrasound probe, a communication quality determination unit that determines a communication quality of the wireless communication on the basis of a ratio of a first number of frames (Continued)

of the ultrasound image received from the ultrasound probe per the unit time to a second number of frames of the ultrasound image skipped per the unit time in the ultrasound probe, and a communication quality display unit that displays information on the communication quality on a monitor.

11 Claims, 4 Drawing Sheets

(56) References Cited

U.S. PATENT DOCUMENTS

2010/0160785 A1 6/2010 Poland et al.
2019/0159760 A1* 5/2019 Ohishi ................. A61B 8/4483
2021/0015461 A1 1/2021 Karasawa
2021/0196243 A1 7/2021 Osumi et al.
2022/0386313 A1* 12/2022 Dickie ................... A61B 8/565
2022/0417164 A1* 12/2022 Fruchter ................. H04L 47/30

FOREIGN PATENT DOCUMENTS

JP 2019-097671 A 6/2019
JP 2021-106871 A 7/2021
WO 2019/198785 A1 10/2019

OTHER PUBLICATIONS

International Preliminary Report on Patentability (Chapter I) and Written Opinion of the International Searching Authority issued in PCT/JP2022/028429; issued Apr. 2, 2024.

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2022/028429 filed on Jul. 22, 2022, which claims priority under 35 U.S.C. § 119(a) to Japanese Patent Application No. 2021-160708 filed on Sep. 30, 2021. The above applications are hereby expressly incorporated by reference, in their entirety, into the present application.

BACKGROUND OF THE INVENTION

1. Field of the Invention

The present invention relates to an ultrasound diagnostic apparatus and a control method of the ultrasound diagnostic apparatus for displaying information on a communication quality of wireless communication in a case where an ultrasound image is transmitted from an ultrasound probe to an apparatus main body via wireless communication.

2. Description of the Related Art

In the related art, in an ultrasound diagnostic apparatus in which an ultrasound probe and an apparatus main body are wirelessly connected, information on a communication quality of wireless communication in a case of transferring the ultrasound image is displayed by the number of antenna bars of an antenna pictograph on the basis of a received signal strength indication (RSSI) value provided from a wireless communication module in the apparatus main body or an S (RSSI value)/N (noise value) ratio.

In the ultrasound diagnostic apparatus, a frame rate is set as one of the scan conditions according to the diagnosis purpose, and ultrasound images are sequentially generated at a constant frame rate set according to the diagnosis purpose. However, in a case where the actual transmission rate of the ultrasound image drops below a transmission rate corresponding to the constant frame rate set according to the diagnosis purpose due to a deterioration in communication quality, the transmission of the ultrasound image is skipped in units of frames.

A communication quality of wireless communication fluctuates from time to time any time according to fading, various disturbances, and the like. In a case where some frames of the ultrasound image is skipped and the ultrasound image is not transferred in real time from the ultrasound probe to the apparatus main body according to the fluctuation of the communication quality, the ultrasound image is not displayed in real time, and the influence of the fluctuation of the communication quality is visible in the ultrasound image. Therefore, it is difficult for a user to make an accurate diagnosis.

Here, for example, there are JP2014-050648A, JP2019-097671A, and JP5727785B as the documents in the related art as references for the present invention.

JP2014-050648A discloses an ultrasound diagnostic apparatus that performs ultrasound scanning at a frame rate corresponding to a transmission condition, and in a case where an index value indicating a communication quality of wireless communication is less than a threshold value, that reduces the frame rate to reduce an amount of data transmitted from an ultrasound probe to an apparatus main body.

JP2019-097671A discloses a photoacoustic probe that determines a communication rate according to a communication quality of wireless communication. In addition, JP2019-097671A also discloses that the amount of data delay, the strength of a wireless signal, a data recall rate, and an error ratio are used as the communication quality.

JP5727785B discloses displaying a signal strength indicator indicating a signal strength of wireless communication between a wireless probe and a host system on an information display of the host system.

SUMMARY OF THE INVENTION

Since the RSSI value has a correlation with the error rate of the wireless communication, information on the communication quality of the wireless communication in the medium to long distance can be appropriately displayed on the basis of the RSSI value.

However, in the ultrasound diagnostic apparatus, a distance between the ultrasound probe and the apparatus main body is short, and the RSSI value is basically high. Therefore, the RSSI value does not dominate the error rate of wireless communication. Therefore, it is not appropriate to display the information on the communication quality of wireless communication at the short distance only on the basis of the RSSI value. In the ultrasound diagnostic apparatus, it is necessary to display the ultrasound image in real time, and thus it is desired to display accurate information on the communication quality of wireless communication.

Therefore, an object of the present invention is to provide an ultrasound diagnostic apparatus and a control method of the ultrasound diagnostic apparatus capable of displaying accurate information on a communication quality of wireless communication in an ultrasound diagnostic apparatus in which an ultrasound probe and an apparatus main body are wirelessly connected.

According to the following configuration, the above object can be achieved.

[1] An ultrasound diagnostic apparatus comprising: an ultrasound probe; and an apparatus main body wirelessly connected to the ultrasound probe, in which the ultrasound probe includes an image generation unit that generates an ultrasound image at a constant frame rate, a frame interval adjustment unit that adjusts a frame interval of the ultrasound image transmitted to the apparatus main body by skipping some frames of the ultrasound image transmitted to the apparatus main body per unit time in accordance with a transmission rate of the ultrasound image, and a probe side communication circuit that transmits the ultrasound image with the adjusted frame interval to the apparatus main body via wireless communication, and the apparatus main body includes a main body side communication circuit that receives the ultrasound image via the wireless communication from the ultrasound probe, a communication quality determination unit that determines a communication quality of the wireless communication on the basis of a ratio of a first number of frames of the ultrasound image received from the ultrasound probe per the unit time to a second number of frames of the ultrasound image skipped per the unit time in the ultrasound probe, and a communication quality display unit that displays information on the communication quality on a monitor.

[2] The ultrasound diagnostic apparatus according to [1], in which the ultrasound probe includes a sequence number assignment unit that assigns sequence numbers to the ultrasound images generated at the constant frame rate in an order of generation of the ultrasound images, and the communication quality determination unit calculates the second number of frames by determining some skipped frames of the ultrasound image on the basis of the sequence numbers.

[3] The ultrasound diagnostic apparatus according to [1] or [2], in which the communication quality determination unit determines the communication quality of the wireless communication on the basis of a moving average value of the ratio of the first number of frames to the second number of frames within a predetermined time.

[4] The ultrasound diagnostic apparatus according to any one of [1] to [3], in which the main body side communication circuit transmits the second number of frames to the ultrasound probe, the probe side communication circuit receives the second number of frames from the apparatus main body, and the frame interval adjustment unit skips some other frames of the ultrasound image transmitted to the apparatus main body per unit time such that the second number of frames received from the apparatus main body is less than a predetermined percentage with respect to the number of frames of the ultrasound image corresponding to the constant frame rate.

[5] The ultrasound diagnostic apparatus according to any one of [1] to [3], in which the main body side communication circuit transmits the second number of frames to the ultrasound probe, the probe side communication circuit receives the second number of frames from the apparatus main body, and the frame interval adjustment unit has a high speed mode in which the ultrasound image is transmitted at a first frame interval and a low speed mode in which the ultrasound image is transmitted at a second frame interval longer than the first frame interval, and switches a mode from the high speed mode to the low speed mode in a case where the second number of frames received from the apparatus main body is equal to or larger than a predetermined percentage with respect to the number of frames of the ultrasound image corresponding to the constant frame rate.

[6] The ultrasound diagnostic apparatus according to any one of [1] to [3], in which the main body side communication circuit transmits the first number of frames and the second number of frames to the ultrasound probe, the probe side communication circuit receives the first number of frames and the second number of frames from the apparatus main body, and the frame interval adjustment unit skips some other frames of the ultrasound image transmitted to the apparatus main body per unit time in accordance with the first number of frames and the second number of frames received from the apparatus main body.

[7] The ultrasound diagnostic apparatus according to any one of [1] to [3], in which the main body side communication circuit transmits the first number of frames and the second number of frames to the ultrasound probe, the probe side communication circuit receives the first number of frames and the second number of frames from the apparatus main body, and the frame interval adjustment unit has a high speed mode in which the ultrasound image is transmitted at a first frame interval and a low speed mode in which the ultrasound image is transmitted at a second frame interval longer than the first frame interval, and selects one of the high speed mode or the low speed mode in accordance with the first number of frames and the second number of frames received from the apparatus main body.

[8] The ultrasound diagnostic apparatus according to any one of [1] to [7], in which the communication quality determination unit determines the communication quality by taking into account a variation in frame intervals of the ultrasound image received from the ultrasound probe per unit time.

[9] An ultrasound diagnostic apparatus comprising: an ultrasound probe; and an apparatus main body wirelessly connected to the ultrasound probe, in which the ultrasound probe includes an image generation unit that generates an ultrasound image at a constant frame rate, a frame interval adjustment unit that adjusts a frame interval of the ultrasound image transmitted to the apparatus main body by skipping some frames of the ultrasound image transmitted to the apparatus main body per unit time in accordance with a transmission rate of the ultrasound image, and a probe side communication circuit that transmits the ultrasound image with the adjusted frame interval to the apparatus main body via wireless communication, and the apparatus main body includes a main body side communication circuit that receives the ultrasound image via the wireless communication from the ultrasound probe, a communication quality determination unit that determines a communication quality of the wireless communication on the basis of a variation in frame intervals of the ultrasound image received from the ultrasound probe per the unit time, and a communication quality display unit that displays information on the communication quality on a monitor.

[10] The ultrasound diagnostic apparatus according to [8] or [9], in which the communication quality determination unit determines the communication quality of the wireless communication on the basis of a moving average value of the variation in the frame intervals of the ultrasound image within a predetermined time.

[11] The ultrasound diagnostic apparatus according to [3] or [10], in which the communication quality determination unit determines that the communication quality is deteriorated in a case where the moving average value is equal to or larger than a predetermined percentage.

[12] The ultrasound diagnostic apparatus according to any one of [1] to [11], in which the main body side communication circuit transmits the communication quality to the ultrasound probe, the probe side communication circuit receives the communication quality from the apparatus main body, and the frame interval adjustment unit skips some other frames of the ultrasound image transmitted to the apparatus main body per unit time in accordance with the communication quality received from the apparatus main body.

[13] A control method of an ultrasound diagnostic apparatus including an ultrasound probe, and an apparatus main body wirelessly connected to the ultrasound probe, the control method comprising: a step of generating an ultrasound image at a constant frame rate via an image generation unit of the ultrasound probe; a step of adjusting a frame interval of the ultrasound image transmitted to the apparatus main body by skipping some frames of the ultrasound image transmitted to the apparatus main body per unit time in accordance with a transmission rate of the ultrasound image via a frame interval adjustment unit of the ultrasound probe; and a step of transmitting the ultrasound image with an adjusted frame interval to the apparatus main body via wireless communication via a probe side communication circuit of the ultrasound probe; and a step of receiving the ultrasound image via the wireless communication from the ultrasound probe via a main body side communication circuit of the apparatus main body; a step of determining a communication quality of the wireless communication on the basis of a ratio of a first number of frames of the ultrasound image received from the ultrasound probe per the unit time to a second number of frames of the ultrasound image skipped per the unit time in the ultrasound probe via a communication quality determination unit of the apparatus main body; and a step of displaying information on the communication quality on a monitor via a communication quality display unit of the apparatus main body.

[14] A control method of an ultrasound diagnostic apparatus including an ultrasound probe, and an apparatus main body wirelessly connected to the ultrasound probe, the control method comprising: a step of generating an ultrasound image at a constant frame rate via an image generation unit of the ultrasound probe; a step of adjusting a frame interval of the ultrasound image transmitted to the apparatus main body by skipping some frames of the ultrasound image transmitted to the apparatus main body in accordance with a transmission rate of the ultrasound image via a frame interval adjustment unit of the ultrasound probe; and a step of transmitting the ultrasound image with an adjusted frame interval to the apparatus main body via wireless communication via a probe side communication circuit of the ultrasound probe; and a step of receiving the ultrasound image via the wireless communication from the ultrasound probe via a main body side communication circuit of the apparatus main body; a step of determining a communication quality of the wireless communication on the basis of a variation in frame intervals of the ultrasound image received from the ultrasound probe per the unit time via a communication quality determination unit of the apparatus main body; and a step of displaying information on the communication quality on a monitor via a communication quality display unit of the apparatus main body.

In the present invention, the communication quality of the wireless communication is determined on the basis of the ratio of the first number of frames to the second number of frames, the variation in the frame intervals of the ultrasound image, or both, and the information on the communication quality of the wireless communication is displayed on the monitor. Accordingly, in the ultrasound diagnostic apparatus that performs wireless communication at a short distance between the ultrasound probe and the apparatus main body, it is possible to display the accurate information on the communication quality of wireless communication on the monitor.

DESCRIPTION OF THE PREFERRED EMBODIMENTS

Hereinafter, an ultrasound diagnostic apparatus and a control method for the ultrasound diagnostic apparatus of the embodiment of the present invention will be described in detail on the basis of suitable embodiments shown in the accompanying drawings.

Figure 1:
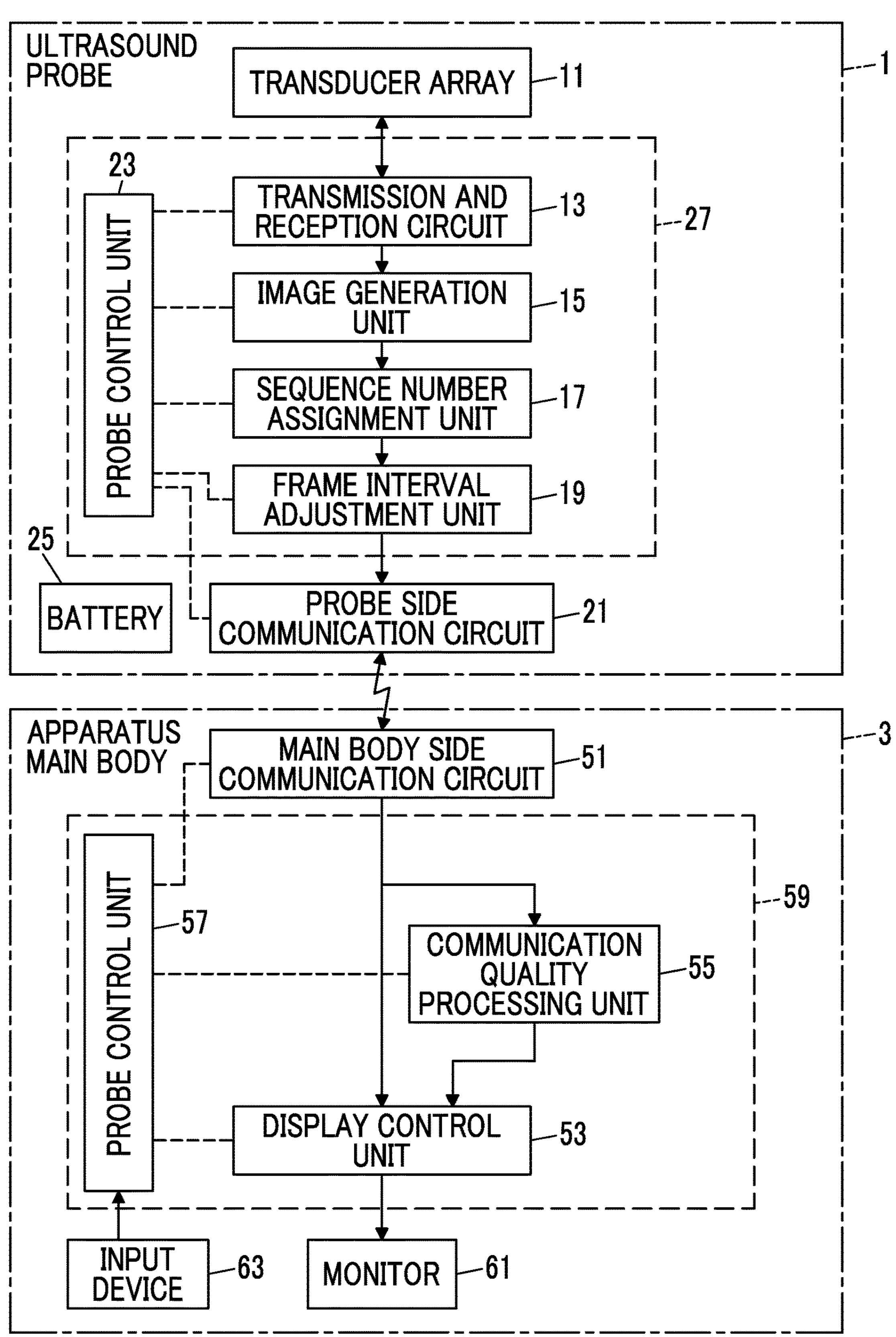
FIG. 1 is a block diagram showing a configuration of an ultrasound diagnostic apparatus of an embodiment of the present invention.

FIG. 1 is a block diagram of an embodiment showing a configuration of the ultrasound diagnostic apparatus of the embodiment of the present invention. The ultrasound diagnostic apparatus shown in FIG. 1 is a handheld ultrasound diagnostic apparatus and comprises an ultrasound probe 1 and an apparatus main body 3 wirelessly connected to the ultrasound probe 1. The ultrasound diagnostic apparatus of the present embodiment is realized by the ultrasound probe 1, the apparatus main body 3, and an application program for ultrasound diagnosis that operates on the apparatus main body 3.

The ultrasound probe 1 scans an examination area of a subject under examination with an ultrasound beam and outputs an ultrasound image of the examination area. As shown in FIG. 1, the ultrasound probe 1 comprises a transducer array 11, a transmission and reception circuit 13, an image generation unit 15, a sequence number assignment unit 17, a frame interval adjustment unit 19, a probe side communication circuit 21, a probe control unit 23, and a battery 25.

The transducer array 11 and the transmission and reception circuit 13 are bidirectionally connected to each other. The image generation unit 15, the sequence number assignment unit 17, the frame interval adjustment unit 19, and the probe side communication circuit 21 are sequentially connected to the transmission and reception circuit 13. A probe control unit 23 is connected to the transmission and reception circuit 13, the image generation unit 15, the sequence number assignment unit 17, the frame interval adjustment unit 19, and the probe side communication circuit 21. In addition, the battery 25 is built in the ultrasound probe 1.

A probe side processor 27 is configured by the transmission and reception circuit 13, the image generation unit 15, the sequence number assignment unit 17, the frame interval adjustment unit 19, and the probe control unit 23.

The transducer array 11 includes a plurality of ultrasound transducers arranged one-dimensionally or two-dimensionally. Each of these transducers transmits an ultrasound wave in accordance with a drive signal supplied from the transmission and reception circuit 13 and outputs an analog reception signal by receiving a reflected wave from the subject under examination.

For example, each transducer is composed of an element obtained by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
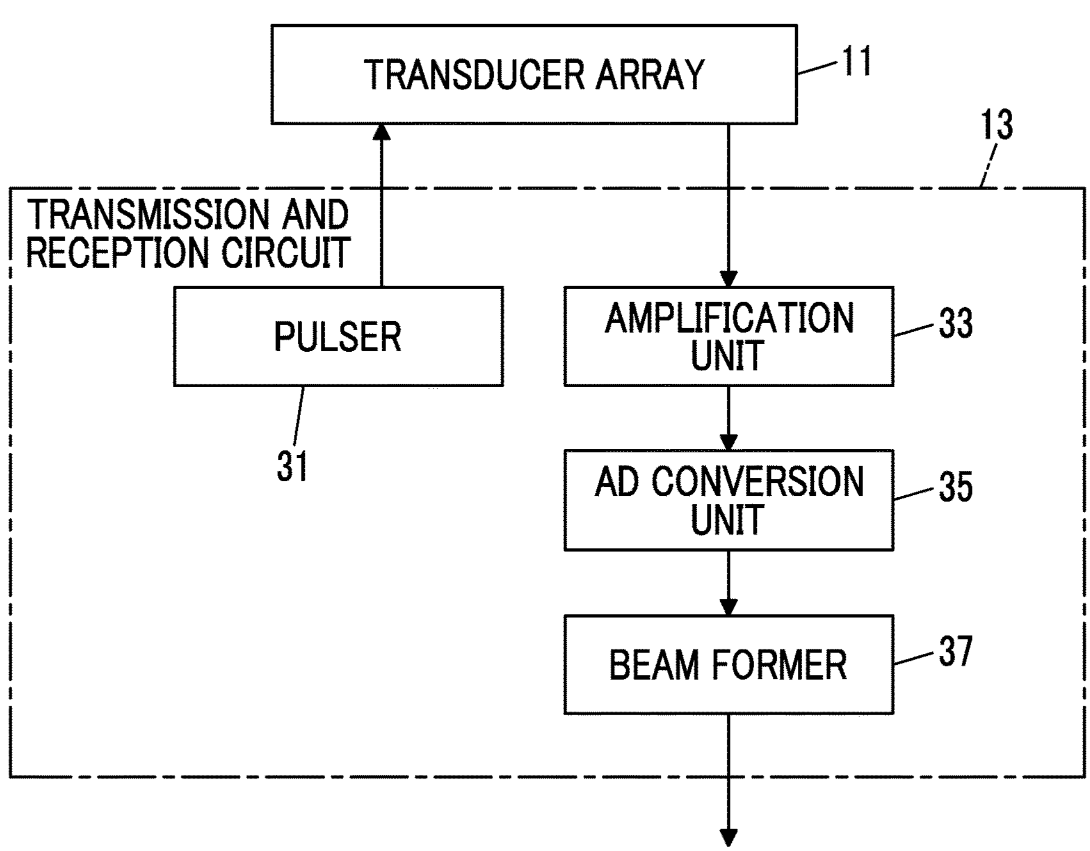
FIG. 2 is a block diagram showing a configuration of a transmission and reception circuit.

The transmission and reception circuit 13, under control of the probe control unit 23, transmits an ultrasound beam from the transducer array 11 and performs reception focus processing on a reception signal output from the transducer array 11 that has received an ultrasound echo, thereby generating a sound ray signal. As shown in FIG. 2, the transmission and reception circuit 13 includes a pulser 31 connected to the transducer array 11, and an amplification unit 33, an analog digital (AD) conversion unit 35, and a beam former 37 that are sequentially connected in series from the transducer array 11.

The pulser 31 includes, for example, a plurality of pulse generators, and performs transmission focus processing of adjusting the amount of delay of each drive signal so that the ultrasound wave transmitted from the plurality of transducers of the transducer array 11 forms an ultrasound beam on the basis of a transmission delay pattern selected by the probe control unit 23 and supplying it to the plurality of transducers. In a case where a pulsed or continuous-wave voltage is applied to the electrodes of the transducer of the transducer array 11 through the transmission focus processing, the piezoelectric body expands and contracts, and a pulsed or continuous-wave ultrasound wave is generated from each of the transducers, whereby the ultrasound beam is formed from a combined wave of these ultrasound waves.

The transmitted ultrasound beam is reflected by a target, for example, a site of the subject under examination, and propagates toward the transducer array 11 of the ultrasound probe 1. Each of the transducers constituting the transducer array 11 expands and contracts by receiving the ultrasound echo propagating toward the transducer array 11 in this manner, generates a reception signal, which is an electrical signal, and outputs the reception signal to the amplification unit 33.

The amplification unit 33 amplifies the analog signal input from each of the transducers constituting the transducer array 11 and transmits the amplified signal to the AD conversion unit 35. The AD conversion unit 35 converts the signal transmitted from the amplification unit 33 into digital reception data and outputs the reception data to the beam former 37.

The beam former 37 performs reception focus processing in which addition is performed by giving delays to respective pieces of the reception data converted by the AD conversion unit 35 according to a sound speed distribution or a sound speed which is set on the basis of the reception delay pattern selected by the probe control unit 23. Through the reception focus processing, a sound ray signal in which each piece of the reception data converted by the AD conversion unit 35 is phased and added and the focus of the ultrasound echo is narrowed down is generated.

Figure 3:
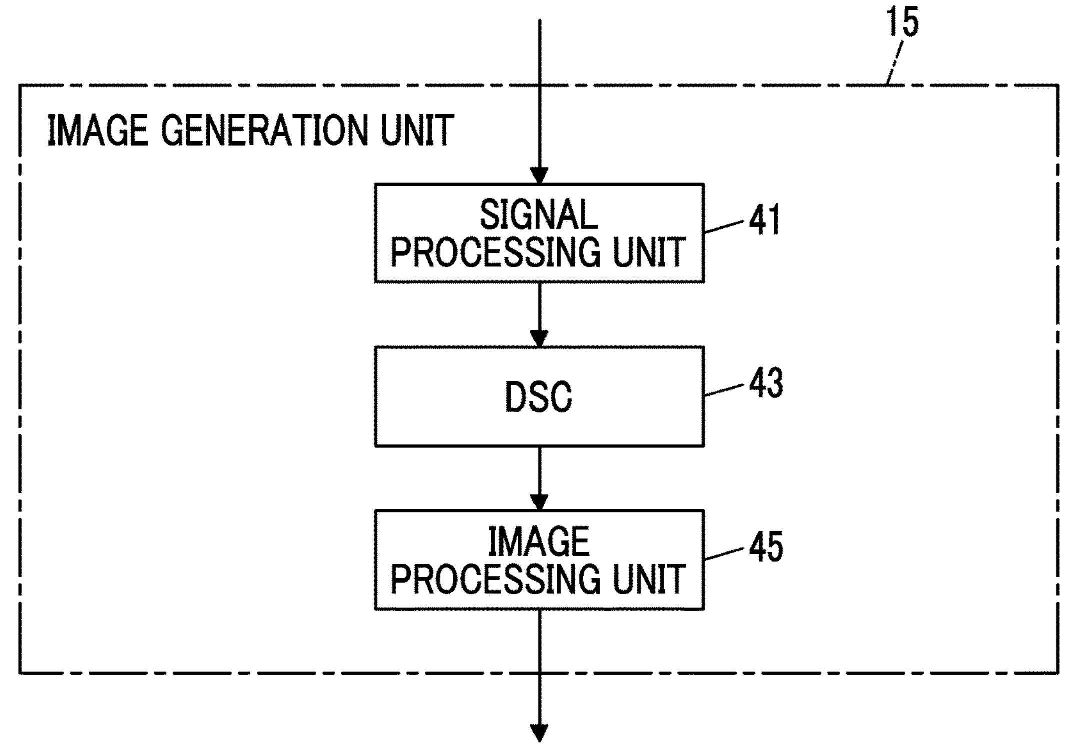
FIG. 3 is a block diagram showing a configuration of an image generation unit.

The image generation unit 15 generates, under the control of the probe control unit 23, an ultrasound image (ultrasound image signal) of an examination area of the subject under examination at a constant frame rate from the sound ray signal obtained by performing transmission and reception of the ultrasound beam to and from the examination area of the subject under examination using the ultrasound probe 1 (more precisely, transducer array 11). As shown in FIG. 3, the image generation unit 15 has a configuration in which a signal processing unit 41, a DSC 43, and an image processing unit 45 are sequentially connected in series.

The frame rate is one of the scan conditions set in advance according to the diagnosis purpose, in other words, preset for the diagnosis purpose, and is set to, for example, 10 Hz in a case where the diagnosis purpose is the examination of the abdomen and the obstetrics. In addition, the frame rate is set to 15 Hz in a case where the diagnosis purpose is the examination of a superficial organ or a blood vessel, 20 Hz in a case where of the examination of a puncture, and 30 Hz in a case of the examination of a heart.

The signal processing unit 41 generates image information data before image formation into an ultrasound image on the basis of the sound ray signal generated by the transmission and reception circuit 13. More specifically, the signal processing unit 41 performs signal processing on the sound ray signal generated by the beam former 37, for example, corrects the attenuation caused by a propagation distance according to the depth of a position where the ultrasound wave is reflected, and then performs envelope detection processing to generate the image information data representing tomographic image information regarding tissues inside the subject under examination.

The digital scan converter (DSC) 43 raster-converts the image information data generated by the signal processing unit 41 into an image signal according to a scanning method of a normal television signal.

The image processing unit 45 performs various types of image processing such as brightness correction, gradation correction, sharpness correction, image size correction, refresh rate correction, scanning frequency correction, and color correction according to a display format of the monitor 61 on the image signal input from the DSC 43 to generate the ultrasound image, and then outputs the ultrasound image, which has been subjected to the image processing, to the sequence number assignment unit 17.

The sequence number assignment unit 17 assigns sequence numbers 1, 2, 3, . . . to the ultrasound images generated by the image generation unit 15 at a constant frame rate in the order of the generation of the ultrasound images, under the control of the probe control unit 23.

The frame interval adjustment unit 19 adjusts a frame interval of the ultrasound image transmitted to the apparatus main body 3 by skipping some frames of the ultrasound image transmitted to the apparatus main body 3 per unit time such as 1 second in accordance with the transmission rate of the ultrasound image via wireless communication, under the control of the probe control unit 23.

The frame interval of the ultrasound image is a time interval from a transmission start time point of the ultrasound image of the frame transmitted from the ultrasound probe 1 to the apparatus main body 3 to a transmission start time point of the ultrasound image of the next transmitted frame. As described above, the communication quality of wireless communication between the ultrasound probe 1 and the apparatus main body 3 fluctuates from time to time according to fading, various disturbances, and the like. Since the transmission rate of the ultrasound image fluctuates according to the fluctuation of the communication quality, the frame interval adjustment unit 19 adjusts the frame interval of the ultrasound image by skipping some frames of the ultrasound image according to the fluctuation of the transmission rate of the ultrasound image.

The frame interval adjustment unit 19 does not skip the frame of the ultrasound image in a case where the transmission rate of the ultrasound image is equal to or higher than a transmission rate corresponding to the frame rate.

On the other hand, in a case where the transmission rate of the ultrasound image is less than the transmission rate corresponding to the frame rate, the frame interval adjustment unit 19 increases the number of frames of the ultrasound image to be skipped as the transmission rate of the ultrasound image is decreased. In other words, the frame interval adjustment unit 19 performs adjustment such that the frame interval of the ultrasound image transmitted to the apparatus main body 3 is long, that is, the number of frames of the ultrasound image transmitted per unit time is reduced, or the frame rate of the wireless communication is reduced by reducing the number of frames of the ultrasound image transmitted from the ultrasound probe 1 to the apparatus main body 3.

The frame interval adjustment unit 19 has, for example, a buffer that stores ultrasound images of one or more frames, and the ultrasound images of the frames stored in the buffer are sequentially transmitted from the ultrasound probe 1 to the apparatus main body 3. In a case where there is a free region of one frame or more in the buffer in accordance with the transmission rate of the ultrasound image, the ultrasound image of the next frame is stored in the buffer. In a case where there is no free region of one frame or more in the buffer, the ultrasound image of the next frame is not stored in the buffer and is skipped.

The probe side communication circuit 21 transmits the ultrasound image of which the frame interval is adjusted by the frame interval adjustment unit 19 to the apparatus main body 3 via wireless communication under the control of the probe control unit 23.

The probe control unit 23 controls each part of the ultrasound probe 1 on the basis of a program and the like stored in advance.

The battery 25 is built in the ultrasound probe 1, and supplies power to each circuit of the ultrasound probe 1.

Next, the apparatus main body 3 is a handheld terminal apparatus such as a smartphone and a tablet personal computer (PC), and receives the ultrasound image from the ultrasound probe 1 and displays the ultrasound image. As shown in FIG. 1, the apparatus main body 3 comprises a main body side communication circuit 51, a display control unit 53, a communication quality processing unit 55, a main body control unit 57, a monitor 61, and an input device 63.

The display control unit 53 and the monitor 61 are sequentially connected in series to the main body side communication circuit 51. In addition, the communication quality processing unit 55 is connected to the main body side communication circuit 51, and the display control unit 53 is connected to the communication quality processing unit 55. The main body control unit 57 is connected to the main body side communication circuit 51, the display control unit 53, and the communication quality processing unit 55, and the main body control unit 57 is connected to the input device 63.

A main body side processor 59 is composed of the display control unit 53, the communication quality processing unit 55, and the main body control unit 57.

In the present embodiment, the probe side communication circuit 21 of the ultrasound probe 1 is wirelessly connected to the main body side communication circuit 51 of the apparatus main body 3 via wireless communication. Accordingly, the ultrasound probe 1 and the apparatus main body 3 are connected to be capable of bidirectionally exchanging information.

The main body side communication circuit 51 receives the ultrasound image from the ultrasound probe 1 via wireless communication under the control of the main body control unit 57. More specifically, the main body side communication circuit 51 receives the ultrasound image transmitted from the probe side communication circuit 21 of the ultrasound probe 1 via wireless communication.

The display control unit 53 displays various types of information on the monitor 61 under the control of the main body control unit 57. For example, the display control unit 53 performs predetermined processing on the ultrasound image received from the ultrasound probe 1 by the main body side communication circuit 51 to display it on the monitor 61, or displays information on the communication quality of the wireless communication on the monitor 61. In addition, the display control unit 53 displays various messages, various operation screens, and the like on the monitor 61.

Under the control of the display control unit 53, the monitor 61 displays various types of information. As described above, the monitor 61 displays not only the ultrasound image but also information on the communication quality, various messages, various operation screens, and the like. Examples of the monitor 61 include a display device such as a liquid crystal display (LCD), and an organic electro-luminescence (EL) display.

Figure 4:
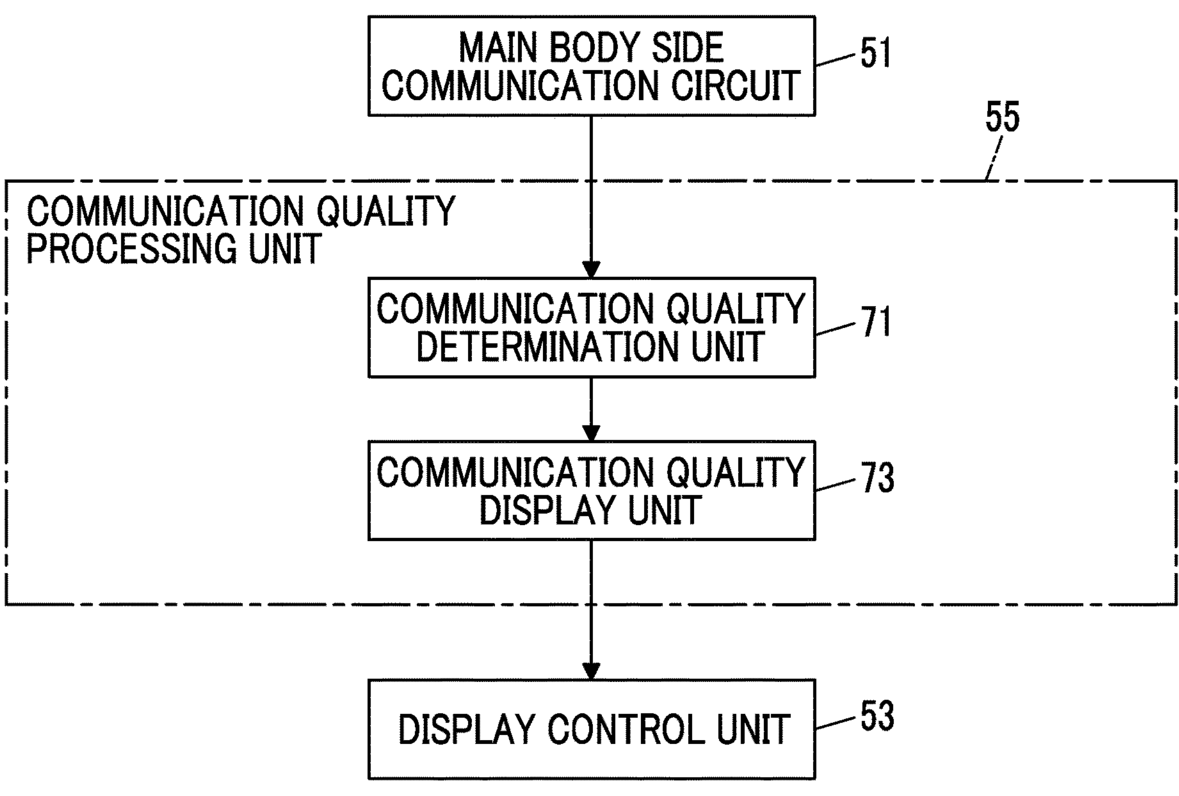
FIG. 4 is a block diagram showing a configuration of a communication quality processing unit.

Under the control of the main body control unit 57, the communication quality processing unit 55 performs various types of processing related to the communication quality of wireless communication, and in the case of the present embodiment, determines and displays the communication quality. As shown in FIG. 4, the communication quality processing unit 55 includes a communication quality determination unit 71 and a communication quality display unit 73.

The communication quality determination unit 71 is connected to the main body side communication circuit 51. The communication quality display unit 73 and the display control unit 53 are sequentially connected to the communication quality determination unit 71.

The communication quality determination unit 71 calculates the first number of frames of the ultrasound image received from the ultrasound probe 1 per unit time by the main body side communication circuit 51 and the second number of frames of the ultrasound image skipped per unit time in the ultrasound probe 1 (more strictly, the frame interval adjustment unit 19), and determines the communication quality of wireless communication on the basis of a ratio of the first number of frames to the second number of frames, for example, (the second number of frames/the first number of frames).

The total value of the first number of frames and the second number of frames is the number of frames of the ultrasound image corresponding to a constant frame rate set according to the diagnosis purpose.

The communication quality determination unit 71 can calculate the first number of frames by, for example, counting the number of frames of the ultrasound image received from the ultrasound probe 1 per unit time by the main body side communication circuit 51 using a counter.

The communication quality determination unit 71 can calculate the second number of frames by determining some skipped frames of the ultrasound image on the basis of the sequence numbers assigned to the ultrasound image by the sequence number assignment unit 17. That is, among the ultrasound images received from the ultrasound probe 1 per unit time by the main body side communication circuit 51, the frame of the ultrasound image from which the sequence number is missing is the skipped frame of the ultrasound image.

The communication quality determination unit 71 can distinguish and determine the communication quality, for example, into a plurality of stages corresponding to the number of antenna bars of the pictogram, on the basis of the ratio of the first number of frames and the second number of frames.

For example, the communication quality determination unit 71 determines that the communication quality is better as the value of the ratio of the first number of frames to the second number of frames is smaller. In other words, the communication quality determination unit 71 determines that the communication quality is better as the number of frames of the ultrasound image transmitted from the ultrasound probe 1 to the apparatus main body 3 per unit time is larger, that is, as the number of frames of the ultrasound image skipped per unit time is smaller.

The communication quality display unit 73 displays the information on the communication quality determined by the communication quality determination unit 71 on the monitor 61 under the control of the display control unit 53.

The communication quality display unit 73 may display a message on the monitor 61 or may display a pictogram on the monitor 61 as the information on the communication quality.

For example, in a case where the information on the communication quality is in three stages of good, normal, and bad, the communication quality display unit 73 displays a message of "communication quality: good", "communication quality: normal", "communication quality: bad", or the like on the monitor according to the communication quality.

For example, in a case where the information on the communication quality is in four stages corresponding to the four antenna bars of the pictogram, the communication quality display unit 73 determines the number of antenna bars according to the communication quality and displays the pictogram of which the number of antenna bars is determined on the monitor 61. For example, in a case where the communication quality is the fourth stage, which is the best communication quality, among the four stages corresponding to the four antenna bars, the pictogram having the four antenna bars is displayed on the monitor 61.

The input device 63 is for the user to perform an input operation to input various instructions, and includes, for example, various buttons, a touch panel for the user to perform a touch operation to input various instructions, and a voice input device for the user to input various instructions with voice.

Figure 5:
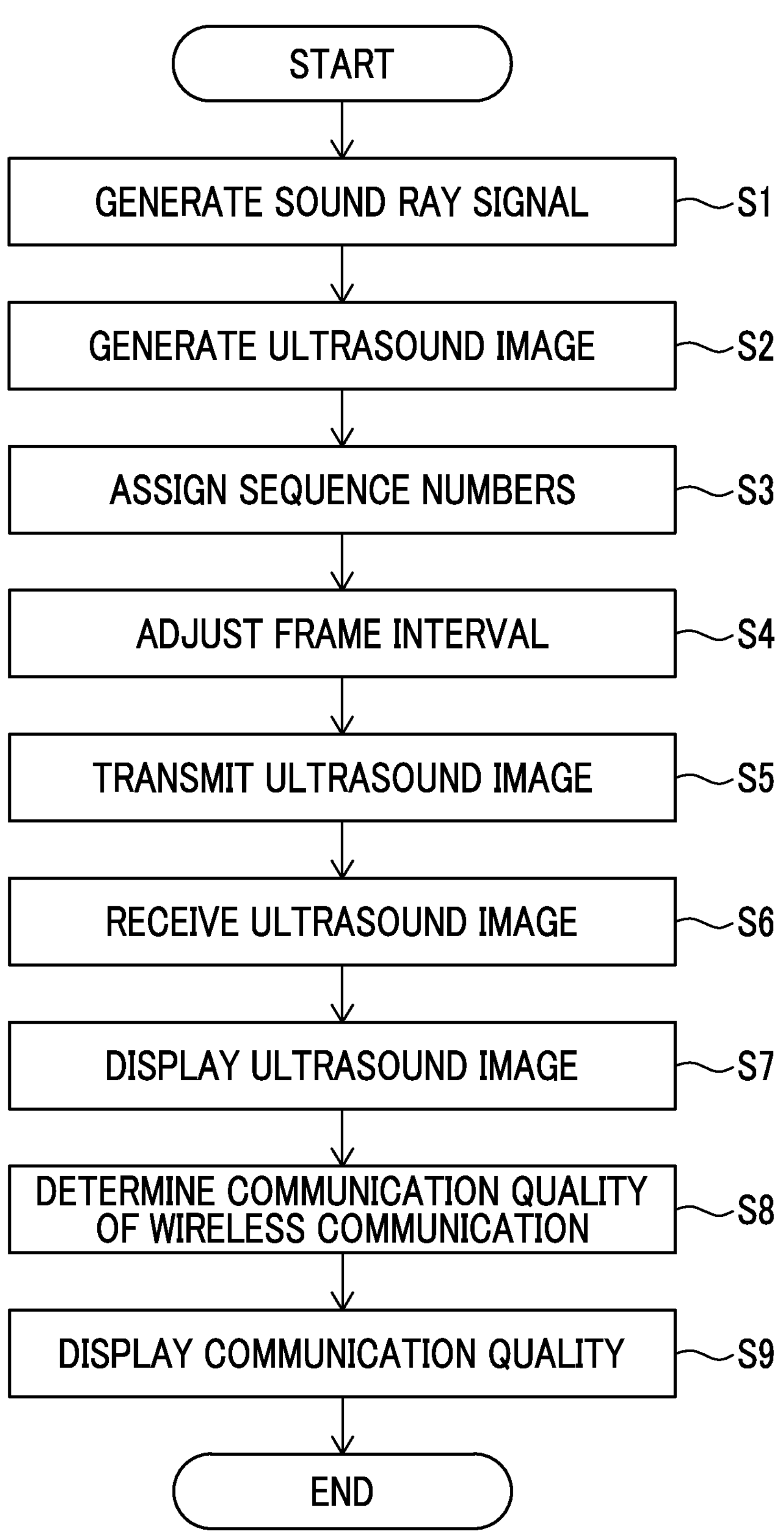
FIG. 5 is a flowchart of an embodiment showing an operation of the ultrasound diagnostic apparatus.

Next, the operation of the ultrasound diagnostic apparatus will be described with reference to the flowchart of FIG. 5.

First, the user selects the diagnosis purpose. For example, in a case where the user selects the examination of the abdomen as the diagnosis purpose, the frame rate is set to 10 Hz as described above.

Subsequently, the user inputs an instruction to start the examination from the input device 63 or the like in a state where the ultrasound probe 1 is in contact with the examination area of the subject under examination. In response to this instruction, the transmission and reception circuit 13 starts the transmission of the ultrasound beam, and the sound ray signal is generated (Step S1).

That is, in the transmission and reception circuit 13, the ultrasound beam is transmitted to the subject under examination from the plurality of transducers of the transducer array 11 in accordance with the drive signal from the pulser 31.

Ultrasound echoes from the subject under examination on the basis of the ultrasound beams transmitted from the pulser 31 are received by each transducer of the transducer array 11, and the reception signal as an analog signal is output from each transducer of the transducer array 11, which has received the ultrasound echo.

The reception signal as the analog signal output from each transducer of the transducer array 11 is amplified by the amplification unit 33 of the transmission and reception circuit 13, and is subjected to AD conversion by the AD conversion unit 35, and thereby the reception data is acquired.

The sound ray signal is generated by performing the reception focus processing on the reception data via the beam former 37.

Subsequently, the image generation unit 15 generates the ultrasound image of the examination area of the subject under examination at a constant frame rate set according to the diagnosis purpose on the basis of the sound ray signal generated by the beam former 37 of the transmission and reception circuit 13 (Step S2).

That is, in the image generation unit 15, various types of signal processing is performed on the sound ray signal generated by the beam former 37 by the signal processing unit 41 to generate the signal representing the tomographic image information related to tissues in the subject under examination as the image signal data before image formation.

The image processing unit 45 performs the raster conversion and further performs various types of image processing on the image signal data generated by the signal processing unit 41 to generate the ultrasound image.

Subsequently, the sequence number assignment unit 17 assigns sequence numbers 1, 2, 3, . . . to the ultrasound images generated by the image generation unit 15 at a constant frame rate in the order of the generation of the ultrasound images (Step S3).

Subsequently, some frames of the ultrasound image transmitted to the apparatus main body 3 per unit time in accordance with the transmission rate of the ultrasound image via wireless communication is skipped and a frame interval of the ultrasound image transmitted to the apparatus main body 3 is adjusted by the frame interval adjustment unit 19 (Step S4).

Subsequently, the ultrasound image in which the frame interval is adjusted by the frame interval adjustment unit 19 is transmitted from the ultrasound probe 1 to the apparatus main body 3 via wireless communication by the probe side communication circuit 21 (Step S5).

Accordingly, in the apparatus main body 3, the ultrasound image transmitted from the probe side communication circuit 21 of the ultrasound probe 1 via wireless communication is received by the main body side communication circuit 51 (Step S6).

Subsequently, the display control unit 53 performs the predetermined processing on the ultrasound image received by the main body side communication circuit 51 and displays the ultrasound image on the monitor 61 (Step S7).

In addition, the communication quality processing unit 55 performs various types of processing related to the communication quality.

That is, in the communication quality processing unit 55, the communication quality determination unit 71 calculates the first number of frames of the ultrasound image received from the ultrasound probe 1 per unit time by the main body side communication circuit 51 and the second number of frames of the ultrasound image skipped per unit time, and determines the communication quality of wireless communication on the basis of a ratio of the first number of frames and the second number of frames (Step S8).

Then, the information on the communication quality determined by the communication quality determination unit 71 is displayed on the monitor 61 by the communication quality display unit 73 (Step S9).

As described above, in the ultrasound diagnostic apparatus according to the present embodiment, the communication quality of wireless communication is determined on the basis of the ratio of the first number of frames to the second number of frames, and the information on the communication quality of wireless communication is displayed on the monitor 61. Accordingly, in the ultrasound diagnostic apparatus that performs wireless communication at a short distance between the ultrasound probe 1 and the apparatus main body 3, it is possible to display the accurate information on the communication quality of wireless communication on the monitor 61.

Instead of the ratio of the first number of frames to the second number of frames, the communication quality determination unit 71 may determine the communication quality of wireless communication on the basis of a variation in the frame interval of the ultrasound image received from the ultrasound probe 1 per unit time by the main body side communication circuit 51, in other words, a variation in the number of frames of the ultrasound image received per unit time, or a variation in the frame rate of the wireless communication.

The communication quality determination unit 71 calculates, for example, a variation of a frame interval of the ultrasound image by calculating an interval value of each frame of the ultrasound image.

In this case, the communication quality determination unit 71 determines that the communication quality is further deteriorated as the variation in the frame interval of the ultrasound image is larger.

Alternatively, the communication quality determination unit 71 may determine the communication quality by taking into account the variation in the frame interval of the ultrasound image described above to the ratio of the first number of frames and the second number of frames. That is, the communication quality determination unit 71 may determine the communication quality of wireless communication on the basis of both the ratio of the first number of frames to the second number of frames and the variation in the frame interval of the ultrasound image.

In this case, the communication quality determination unit 71 determines that the communication quality is further deteriorated as the value of the ratio of the first number of frames to the second number of frames is larger and the variation in the frame interval of the ultrasound image is larger.

The communication quality determination unit 71 may obtain, for example, a moving average value of the ratio of the first number of frames to the second number of frames within a predetermined time, a moving average value of a variation in frame interval of the ultrasound image within the predetermined time, or a moving average value of both of the moving average values, and determine the communication quality on the basis of the moving average value. The predetermined time is, for example, 10 seconds or longer and 1 minute or shorter, and is preferably 10 seconds or 30 seconds.

In this case, the communication quality determination unit 71 determines, for example, that the communication quality is deteriorated in a case where the moving average value increases by a predetermined percentage or more. The predetermined percentage is, for example, 5% or more and 10% or less, and is preferably 5% or 10%.

The communication quality determination unit 71 may determine the communication quality of wireless communication by taking into account the RSSI value provided from the main body side communication circuit 51. For example, the communication quality determination unit 71 may determine the communication quality by taking into account the RSSI value to the ratio of the first number of frames to the second number of frames, may determine the communication quality by taking into account the RSSI value to the variation in the frame interval of the ultrasound image, or may determine the communication quality by taking into account the RSSI value to both the ratio of the first number of frames to the second number of frames and the variation in the frame interval of the ultrasound image.

In this case, the communication quality determination unit 71 determines that the communication quality is better as the value of the ratio of the first number of frames to the second number of frames is smaller, the variation in the frame interval of the ultrasound image is smaller, and the RSSI value is higher. Moreover, the communication quality determination unit 71 determines the communication quality by integrating the ratio of the first number of frames to the second number of frames, the variation in the frame interval of the ultrasound image, and the RSSI value.

The communication quality determination unit 71 can determine a cause of the fluctuation in the communication quality by determining the communication quality by taking into account the RSSI value. In a case where the RSSI value is low, the cause of the fluctuation of the communication quality is dominant by the RSSI value, and in a case where the RSSI value is high, the cause of the fluctuation of the communication quality is dominant by factors other than the RSSI value. For example, in a case where the RSSI value is low, it can be determined that the cause of the deterioration in the communication quality is the decrease in the signal strength of the radio wave. On the other hand, in a case where the RSSI value is high, it can be determined that the cause of the deterioration in the communication quality is a cause other than the signal strength of the radio wave.

In a case where the RSSI value drops below a predetermined threshold value, a message notifying the user that the signal strength of the radio wave is weak may be displayed on the monitor 61, the message may be voiced from the speaker by voice, or both of the message and the voice may be used.

The frame interval adjustment unit 19 may control the amount of frame skipping by systematically skipping some other frames of the ultrasound image in accordance with the communication quality fed back from the apparatus main body 3 to the ultrasound probe 1, separately from some frames of the ultrasound image that are skipped in accordance with the transmission rate of the ultrasound image.

In this case, the communication quality determined by the communication quality determination unit 71 is transmitted to the ultrasound probe 1 by the main body side communication circuit 51, and accordingly, the communication quality is received from the apparatus main body 3 by the probe side communication circuit 21.

Then, the frame interval adjustment unit 19 systematically skips some other frames of the ultrasound image transmitted to the apparatus main body 3 per unit time in accordance with the communication quality received from the apparatus main body 3 by the probe side communication circuit 21.

The frame interval adjustment unit 19 skips more frames of the ultrasound image as the communication quality deteriorates. Accordingly, the frame interval of the ultrasound image is adjusted, and the frame rate of the wireless communication is lowered.

Even in a case where some other frames of the ultrasound image is systematically skipped in accordance with the communication quality by the frame interval adjustment unit 19, as described above, some frames of the ultrasound image is skipped in accordance with the transmission rate of the ultrasound image.

Instead of the communication quality, the frame interval adjustment unit 19 may control the amount of frame skipping by systematically skipping some other frames of the ultrasound image in accordance with the second number of frames, that is, the number of frames of the ultrasound image skipped per unit time.

In this case, the second number of frames is transmitted to the ultrasound probe 1 by the main body side communication circuit 51, and accordingly, the second number of frames is received from the apparatus main body 3 by the probe side communication circuit 21.

Then, the frame interval adjustment unit 19 systematically skips some other frames of the ultrasound image transmitted to the apparatus main body 3 per unit time such that the second number of frames received from the apparatus main body 3 by the probe side communication circuit 21 is less than a predetermined percentage with respect to the number of frames of the ultrasound image corresponding to the constant frame rate set in accordance with the diagnosis purpose.

In addition, the frame interval adjustment unit 19 can control the amount of frame skipping by systematically skipping some other frames of the ultrasound image according to the first number of frames and the second number of frames, that is, the number of frames of the ultrasound image received from the ultrasound probe 1 per unit time and the number of frames of the ultrasound image skipped per unit time.

In this case, the first number of frames and the second number of frames are transmitted to the ultrasound probe 1 by the main body side communication circuit 51, and accordingly, the first number of frames and the second number of frames are received from the apparatus main body 3 by the probe side communication circuit 21.

Then, the frame interval adjustment unit 19 systematically skips some other frames of the ultrasound image transmitted to the apparatus main body 3 per unit time in accordance with, for example, a ratio of the first number of frames to the second number of frames, on the basis of the first number of frames and the second number of frames received from the apparatus main body 3 by the probe side communication circuit 21.

Alternatively, the frame interval adjustment unit 19 may have a high speed mode in which the ultrasound image is transmitted at a first frame interval and a low speed mode in which the ultrasound image is transmitted at a second frame interval longer than the first frame interval, and may switch the mode between the high speed mode and the low speed mode in accordance with the second number of frames.

In this case, the second number of frames is transmitted to the ultrasound probe 1 by the main body side communication circuit 51, and accordingly, the second number of frames is received from the apparatus main body 3 by the probe side communication circuit 21.

Then, in a case where the second number of frames received from the apparatus main body 3 by the probe side communication circuit 21 is equal to or larger than a predetermined percentage, the frame interval adjustment unit 19 switches the mode to a low speed mode from a high speed mode. On the other hand, in a case where the second number of frames received from the apparatus main body 3 by the probe side communication circuit 21 is less than the predetermined percentage, the frame interval adjustment unit 19 switches the mode to the high speed mode from the low speed mode.

In this way, in a case where the probe side communication circuit 21 switches between the low speed mode and the high speed mode, the frame rate of the ultrasound image generation in the image generation unit 15 can be changed in addition to switching between the low speed mode and the high speed mode.

In addition, the frame interval adjustment unit 19 can be configured to select one of the low speed mode and the high speed mode according to the first number of frames and the second number of frames, that is, the number of frames of the ultrasound image received from the ultrasound probe 1 per unit time and the number of frames of the ultrasound image skipped per unit time.

In this case, the first number of frames and the second number of frames are transmitted to the ultrasound probe 1 by the main body side communication circuit 51, and accordingly, the first number of frames and the second number of frames are received from the apparatus main body 3 by the probe side communication circuit 21.

Then, the frame interval adjustment unit 19 selects, for example, one of the high speed mode and the low speed mode in accordance with, for example, the ratio of the first number of frames to the second number of frames on the basis of the first number of frames and the second number of frames received from the apparatus main body 3 by the probe side communication circuit 21.

Even in a case where some other frames of the ultrasound image are systematically skipped in accordance with the second number of frames by the frame interval adjustment unit 19 or in a case where the high speed mode and the low speed mode are switched, some frames of the ultrasound image is similarly skipped in accordance with the transmission rate of the ultrasound image.

In addition, the frame interval adjustment unit 19 may have three or more modes including two modes of the high speed mode and the low speed mode, but preferably has two modes or three modes.

As described above, by feeding back the information on the basis of the ultrasound image received from the ultrasound probe 1, such as the communication quality and the second number of frames, to the ultrasound probe 1, the frame interval of the ultrasound image can be adjusted in the frame interval adjustment unit 19, and the frame rate of the wireless communication can be systematically reduced. Accordingly, since it is possible to reduce the fluctuation in the number of frames of the ultrasound image to be skipped in accordance with the transmission rate of the ultrasound image and to reduce the fluctuation in the frame interval of the ultrasound images, it is possible to reduce the visibility of the influence of the fluctuation in the communication quality in the ultrasound images.

The present invention is not limited to a handheld ultrasound diagnostic apparatus and can also be similarly applied to a stationary ultrasound diagnostic apparatus or a portable ultrasound diagnostic apparatus in which the apparatus main body is realized by a laptop type terminal apparatus as long as wireless communication is performed between the ultrasound probe 1 and the apparatus main body 3.

In the apparatus according to the embodiment of the present invention, a hardware configuration of a processing unit that executes various types of processing of the transmission and reception circuit 13, the image generation unit 15, the sequence number assignment unit 17, the frame interval adjustment unit 19, the probe control unit 23, the display control unit 53, the communication quality processing unit 55, the main body control unit 57, and the like may be dedicated hardware or may be various processors or computers that execute a program. In addition, a hardware configuration of the reference image memories 64 and 64B and the like may be dedicated hardware or may be a memory such as a semiconductor memory or a storage device such as a hard disk drive (HDD) and a solid state drive (SSD).

The various processors include a central processing unit (CPU), which is a general-purpose processor that executes software (program) and functions as the various processing units, a programmable logic device (PLD), which is a processor whose circuit configuration can be changed after manufacture, such as a field programmable gate array (FPGA), and a dedicated electric circuit, which is a processor having a circuit configuration that is designed for exclusive use in order to execute specific processing, such as an application specific integrated circuit (ASIC).

One processing unit may be configured by using one of the various processors or may be configured by using a combination of two or more processors of the same type or different types, for example, a combination of a plurality of FPGAs or a combination of an FPGA and a CPU. In addition, a plurality of processing units may be configured by using one of various processors, or two or more of the plurality of processing units may be collectively configured by using one processor.

For example, first, as represented by a computer, such as a client and a server, there is a form in which one processor is configured by using a combination of one or more CPUs and software and this processor functions as the plurality of processing units. In addition, as represented by a system on chip (SoC) or the like, there is a form in which the processor is used in which the functions of the entire system which includes the plurality of processing units are implemented by a single integrated circuit (IC) chip.

Furthermore, the hardware configuration of these various processors is, more specifically, an electric circuit (circuitry) in which circuit elements, such as semiconductor elements, are combined.

In addition, the method according to the embodiment of the present invention can be implemented, for example, by a program for causing a computer to execute each of the steps thereof. In addition, a computer-readable recording medium on which the program is recorded can be provided.

Although the present invention has been described in detail above, the present invention is not limited to the embodiment described above, and it is needless to say that various improvements or changes may be made without departing from the gist of the present invention.

EXPLANATION OF REFERENCES

1: ultrasound probe
3: apparatus main body
11: transducer array
13: transmission and reception circuit
15: image generation unit
17: sequence number assignment unit
19: frame interval adjustment unit
21: probe side communication circuit
23: probe control unit
25: battery
27: probe side processor
31: pulser
33: amplification unit
35: AD conversion unit
37: beam former
41: signal processing unit
43: DSC
45: image processing unit
51: main body side communication circuit
53: display control unit
55: communication quality processing unit
57: main body control unit
59: main body side processor
61: monitor
63: input device
71: communication quality determination unit
73: communication quality display unit

What is claimed is:

1. An ultrasound diagnostic apparatus comprising:

an ultrasound probe; and an apparatus main body wirelessly connected to the ultrasound probe, wherein the ultrasound probe includes a probe side processor, and a probe side communication circuit, the probe side processor is configured to generate ultrasound images at a constant frame rate, to assign sequence numbers to the ultrasound images generated at the constant frame rate in an order of generation of the ultrasound images, and to adjust a frame interval of the ultrasound image transmitted to the apparatus main body by skipping transmission of some frames of the ultrasound image to the apparatus main body per unit time in accordance with a transmission rate of the ultrasound image, wherein the probe side communication circuit transmits the ultrasound image with the adjusted frame interval to the apparatus main body via wireless communication, and the apparatus main body includes a main body side communication circuit that receives the ultrasound image via the wireless communication from the ultrasound probe, a main body side processor, and a monitor, and the main body side processor is configured to calculate a second number of frames of the ultrasound image skipped from transmission to the apparatus main body per the unit time in the ultrasound probe by determining a frame of the ultrasound image from which the sequence number is missing among the ultrasound images received by the main body side communication circuit is the frame of the ultrasound image skipped from transmission to the apparatus main body, and to determine a communication quality of the wireless communication on the basis of both a ratio of a first number of frames of the ultrasound image received from the ultrasound probe per the unit time to the calculated second number of frames and a variation in frame intervals of the ultrasound image received from the ultrasound probe per the unit time, and to display information on the communication quality on the monitor.

2. The ultrasound diagnostic apparatus according to claim 1, wherein the main body side processor is configured to determine the communication quality of the wireless communication on the basis of a moving average value of the ratio of the first number of frames to the second number of frames within a predetermined time.

3. The ultrasound diagnostic apparatus according to claim 2, wherein the main body side processor is configured to determine that the communication quality is deteriorated in a case where the moving average value is equal to or larger than a predetermined percentage.

4. The ultrasound diagnostic apparatus according to claim 1, wherein the main body side communication circuit transmits the second number of frames to the ultrasound probe, the probe side communication circuit receives the second number of frames from the apparatus main body, and the probe side processor is configured to skip some other frames of the ultrasound image transmitted to the apparatus main body per unit time such that the second number of frames received from the apparatus main body is less than a predetermined percentage with respect to a number of frames of the ultrasound image corresponding to the constant frame rate.

5. The ultrasound diagnostic apparatus according to claim 1, wherein the main body side communication circuit transmits the second number of frames to the ultrasound probe, the probe side communication circuit receives the second number of frames from the apparatus main body, and the probe side processor is configured to have a high speed mode in which the ultrasound image is transmitted at a first frame interval and a low speed mode in which the ultrasound image is transmitted at a second frame interval longer than the first frame interval, and to switch a mode from the high speed mode to the low speed mode in a case where the second number of frames received from the apparatus main body is equal to or larger than a predetermined percentage with respect to the number of frames of the ultrasound image corresponding to the constant frame rate.

6. The ultrasound diagnostic apparatus according to claim 1, wherein the main body side communication circuit transmits the first number of frames and the second number of frames to the ultrasound probe, the probe side communication circuit receives the first number of frames and the second number of frames from the apparatus main body, and the probe side processor is configured to skip some other frames of the ultrasound image transmitted to the apparatus main body per unit time in accordance with the first number of frames and the second number of frames received from the apparatus main body.

7. The ultrasound diagnostic apparatus according to claim 1, wherein the main body side communication circuit transmits the first number of frames and the second number of frames to the ultrasound probe, the probe side communication circuit receives the first number of frames and the second number of frames from the apparatus main body, and the probe side processor is configured to have a high speed mode in which the ultrasound image is transmitted at a first frame interval and a low speed mode in which the ultrasound image is transmitted at a second frame interval longer than the first frame interval, and to select one of the high speed mode or the low speed mode in accordance with the first number of frames and the second number of frames received from the apparatus main body.

8. The ultrasound diagnostic apparatus according to claim 1, wherein the main body side processor is configured to determine the communication quality of the wireless communication on the basis of a moving average value of the variation in the frame intervals of the ultrasound image within a predetermined time.

9. The ultrasound diagnostic apparatus according to claim 8, wherein the main body side processor is configured to determine that the communication quality is deteriorated in a case where the moving average value is equal to or larger than a predetermined percentage.

10. The ultrasound diagnostic apparatus according to claim 1, wherein the main body side communication circuit transmits the communication quality to the ultrasound probe, the probe side communication circuit receives the communication quality from the apparatus main body, and the probe side processor is configured to skip some other frames of the ultrasound image transmitted to the apparatus main body per unit time in accordance with the communication quality received from the apparatus main body.

11. A control method of an ultrasound diagnostic apparatus including an ultrasound probe, and an apparatus main body wirelessly connected to the ultrasound probe, the control method comprising:

a step of generating an ultrasound image at a constant frame rate in the ultrasound probe;

a step of assigning sequence numbers to the ultrasound images in an order of generation of the ultrasound images in the ultrasound probe;

a step of adjusting a frame interval of the ultrasound image transmitted to the apparatus main body by skipping transmission of some frames of the ultrasound image to the apparatus main body per unit time in accordance with a transmission rate of the ultrasound image in the ultrasound probe; and a step of transmitting the ultrasound image with an adjusted frame interval from the ultrasound probe to the apparatus main body via wireless communication;

a step of receiving the ultrasound image via the wireless communication from the ultrasound probe in the apparatus main body;

a step of calculating a second number of frames of the ultrasound image skipped from transmission to the apparatus main body per the unit time in the ultrasound probe by determining a frame of the ultrasound image from which the sequence number is missing among the ultrasound images received from the ultrasound probe is the frame of the ultrasound image skipped from transmission to the apparatus main body in the apparatus main body;

a step of determining a communication quality of the wireless communication on the basis of both a ratio of a first number of frames of the ultrasound image received from the ultrasound probe per the unit time to the calculated second number of frames of the ultrasound image and a variation in frame intervals of the ultrasound image received from the ultrasound probe per the unit time in the apparatus main body; and a step of displaying information on the communication quality on a monitor in the apparatus main body.

* * * * *